(12) United States Patent
Arjunan et al.

(10) Patent No.: US 10,259,770 B2
(45) Date of Patent: Apr. 16, 2019

(54) PROCESS FOR THE PREPARATION OF ETHACRYNIC ACID

(71) Applicant: Strides Shasun Limited, Chennai (IN)

(72) Inventors: Sankar Arjunan, Chennai (IN); Dhanapal Ramu, Omalur Taluk (IN); Sasidaran Manjiny, Periyakalapet (IN)

(73) Assignee: Strides Shasun Limited, Chennai (IN)

( * ) Notice: Subject to any disclaimer, the term of this patent is extended or adjusted under 35 U.S.C. 154(b) by 0 days.

(21) Appl. No.: 15/790,570

(22) Filed: Oct. 23, 2017

(65) Prior Publication Data

US 2018/0111890 A1    Apr. 26, 2018

(30) Foreign Application Priority Data

Oct. 22, 2016   (IN) .............................. 201641036189

(51) Int. Cl.
| | | |
|---|---|---|
| *C07C 51/377* | (2006.01) | |
| *C07C 221/00* | (2006.01) | |
| *C07C 51/41* | (2006.01) | |
| *C07C 211/03* | (2006.01) | |
| *C07C 59/215* | (2006.01) | |
| *C07C 51/43* | (2006.01) | |
| *C07C 51/02* | (2006.01) | |

(52) U.S. Cl.
CPC ............ *C07C 51/377* (2013.01); *C07C 51/02* (2013.01); *C07C 51/41* (2013.01); *C07C 51/43* (2013.01); *C07C 59/215* (2013.01); *C07C 211/03* (2013.01); *C07C 221/00* (2013.01); C07B 2200/13 (2013.01)

(58) Field of Classification Search
CPC ....... C07C 221/00; C07C 51/43; C07C 59/90; C07C 51/02; C07C 211/03; C07C 225/16; C07C 51/377; C07C 51/41; C07C 59/215; C07B 2200/13
See application file for complete search history.

(56) References Cited

U.S. PATENT DOCUMENTS

| | | | | |
|---|---|---|---|---|
| 3,255,241 A | * | 6/1966 | Schultz ................. | A61K 31/19 544/101 |
| 3,322,821 A | | 5/1967 | Cragoe, Jr. | |
| 3,479,402 A | | 11/1969 | Cragoe, Jr. | |

FOREIGN PATENT DOCUMENTS

WO    WO2016/189549    * 12/2016

OTHER PUBLICATIONS

Kaeppler et al.; "A New Lead for Nonpeptidic Active-Site-Directed Inhibitors of the Severe Acute Respiratory Syndrome Coronavirus Main Protease Discovered by a Combination of Screening and Docking Methods"; J. Med. Chem.; 2005; pp. 6832-6842; vol. 48.
Yarwood et al.; "Liquid Chromatographic Analysis of Ethacrynic Acid and Degradation Products in Pharmaceutical Systems"; Journal of Pharmaceutical Sciences; 1985; pp. 220-223; vol. 74:2.

* cited by examiner

*Primary Examiner* — Jafar F Parsa
*Assistant Examiner* — Blaine G Doletski
(74) *Attorney, Agent, or Firm* — The Webb Law Firm

(57) ABSTRACT

The invention provides an improved process for preparing Ethacrynic acid of formula I, including the steps of: (a) reacting 4-butyryl-2,3-dichloro-phenoxy acetic acid of formula II with dimethylamine or its salt to obtain [2,3-dichloro-4-(2-dimethylaminomethylbutyryl)phenoxy] acetic acid of formula III or its salt; (b) hydrolyzing [2,3-dichloro-4-(2-dimethylaminomethylbutyryl)phenoxy] acetic acid hydrochloride of formula III obtained in step a) with t-butyl amine to obtain t-butyl amine salt of Ethacrynic acid; (c) acidifying the t-butyl amine salt of Ethacrynic acid formed in step b) to obtain Ethacrynic acid of formula I; and (d) optionally purifying the obtained Ethacrynic acid with a solvent mixture of alkyl acetate and hydrocarbon solvent. The invention also provides crystalline t-butylamine salt of Ethacrynic acid and process thereof. Also provide compound Ethacrynic acid having a purity of greater than or equal to 99% and a composition including the compound.

3 Claims, 1 Drawing Sheet

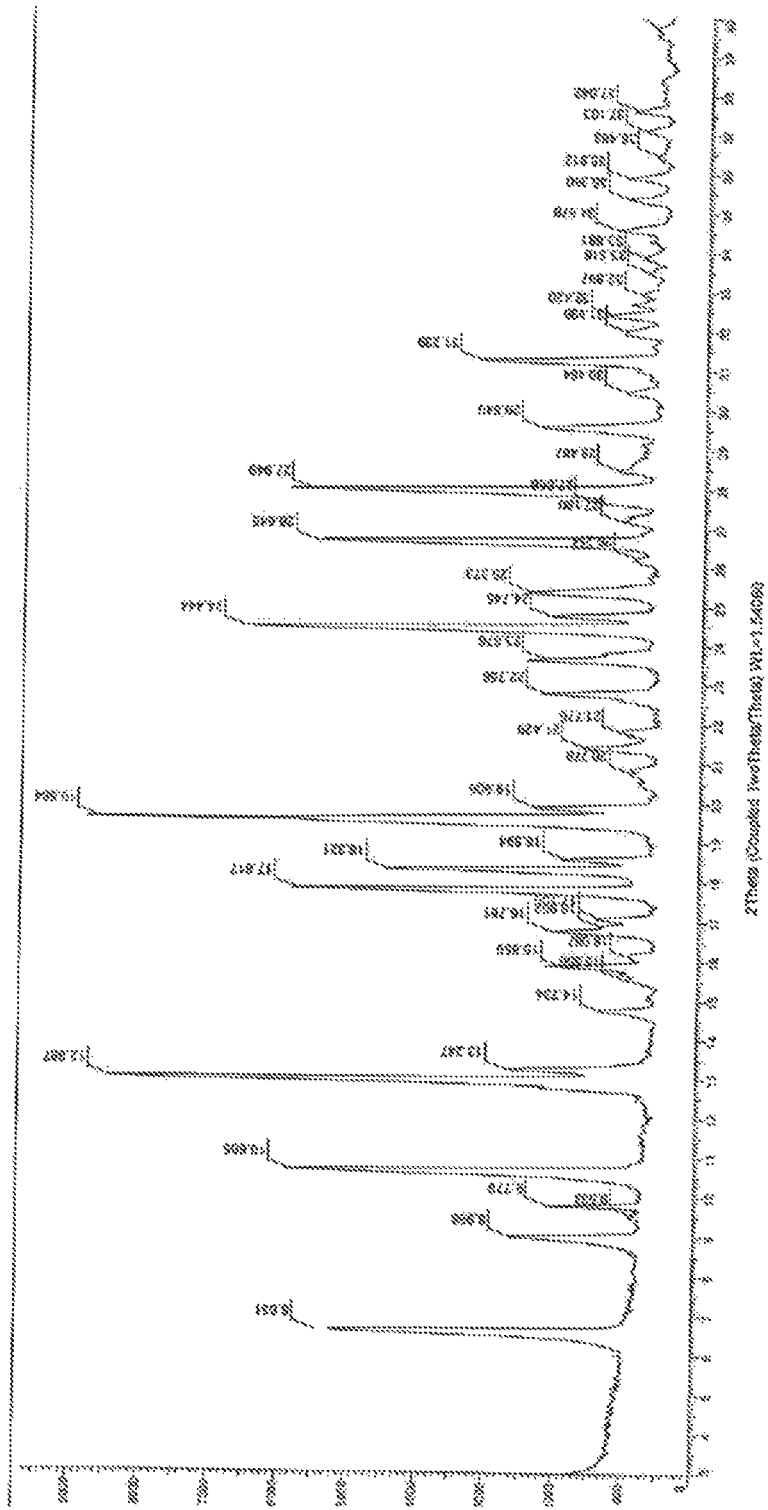

PROCESS FOR THE PREPARATION OF ETHACRYNIC ACID

CROSS-REFERENCE TO RELATED APPLICATION

This application claims priority to Indian Patent Application No. 201641036189 filed Oct. 22, 2016, the disclosure of which is hereby incorporated in its entirety by reference.

BACKGROUND OF THE INVENTION

Field of the Invention

The present invention relates to an improved process for the preparation of Ethacrynic acid and a novel salt of Ethacrynic acid that is employed during the preparation of Ethacrynic acid. The present invention further relates to provide a process for the preparation of crystalline form of novel salt of Ethacrynic acid.

Description of Related Art

Ethacrynic acid is chemically known as [2,3-dichloro-4-(2-methylene-1-oxobutyl) phenoxy] acetic acid and is represented by a compound of structural formula I as mentioned below.

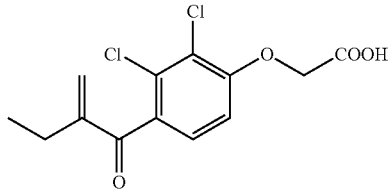

Formula I

Ethacrynic acid is a potent diuretic and is marketed under the brand name 'Edecrin'. Ethacrynic acid was first disclosed in U.S. Pat. No. 3,255,241 and the process for preparing Ethacrynic acid was disclosed in this Patent is shown below:

The above-mentioned process for preparing Ethacrynic acid involves the steps of hydrolysing the intermediate 2,3-dichloro-4-[2-dimethylaminomethyl]butyryl-phenoxy acetic acid hydrochloride with sodium bicarbonate solution to obtain sodium ethacrynate; followed by acidification of the solution containing sodium ethacrynate by hydrochloric acid to yield Ethacrynic acid.

The Patents U.S. Pat. No. 3,322,821 and U.S. Pat. No. 3,479,402 also discloses the preparation of Ethacrynic acid involving the acidification of the solution containing sodium ethacrynate to yield Ethacrynic acid.

The Publication entitled "A New Lead for Nonpeptidic Active-Site-Directed Inhibitors of the Severe Acute Respiratory Syndrome Coronavirus Main Protease Discovered by a Combination of Screening and Docking Methods" by Ulrich Kaeppler et al, Journal of Medicinal Chemistry, 2005, Vol. 1, No. 4 discloses the potassium carbonate instead sodium bicarbonate during the hydrolysis of 2,3-dichloro-4-[2-dimethylaminomethyl]butyryl-phenoxy acetic acid hydrochloride resulting potassium Ethacrynate followed by acidification to yield Ethacrynic acid.

The above processes employ potassium carbonate or sodium bicarbonate as a base for hydrolysis of [2,3-dichloro-4-[2-dimethylaminomethyl butyrylphenoxy acetic acid hydrochloride to ethacrynic acid.

The publication entitled "Liquid chromatographic analysis of ethacrynic acid and degradation products in pharmaceutical systems" by Journal of Pharmaceutical Sciences Vol. 74, No. 2, 1985 states that heating ethacrynic acid in alkali medium results in dimeric derivative of ethacrynic acid as shown below:

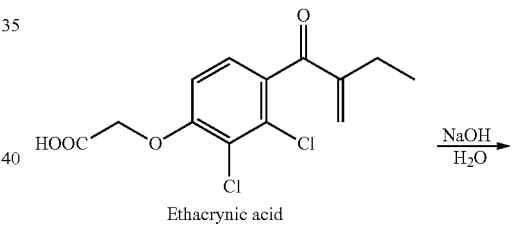

Ethacrynic acid

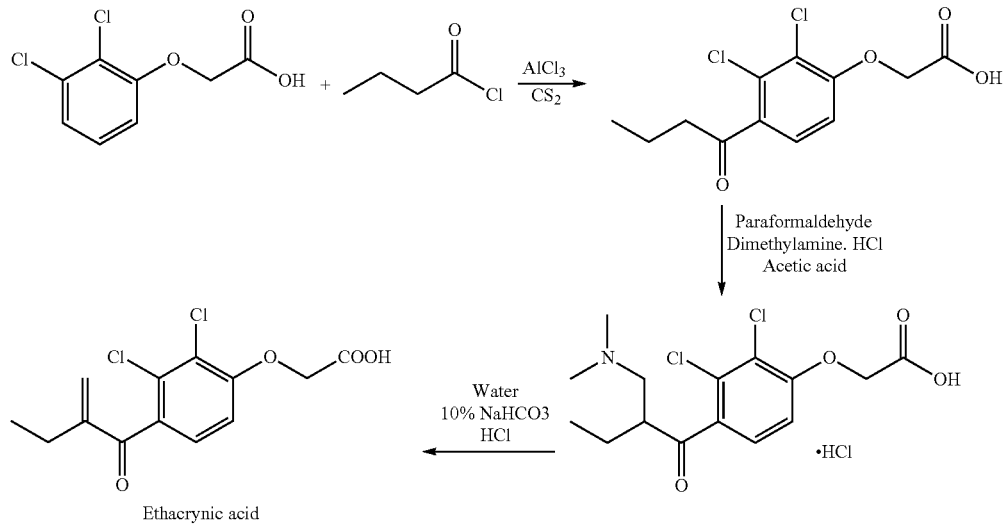

Ethacrynic acid

-continued

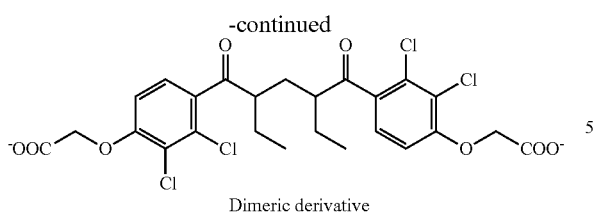

Dimeric derivative

The inventors of present invention have also observed that the Ethacrynic acid formed with processes reported in literature results in high level of dimeric impurity. The dimeric impurity could be formed during the hydrolysis of intermediate 2,3-dichloro-4-[2-dimethylaminomethyl]butyryl-phenoxy acetic acid hydrochloride in the alkali medium due to degradation. The formation of this impurity decreases the quality and yields of the final Ethacrynic acid API.

Hence there is need to improve the process for the preparation of Ethacrynic acid that would be more convenient and suitable for large scale manufacture with better yield and desired quality.

SUMMARY OF THE INVENTION

One objective of the present invention is to provide an improved process for preparing Ethacrynic acid with better yield and high purity that is simple and economically viable.

Another objective of the present invention is to provide a novel process for preparing Ethacrynic acid from t-butylamine salt of Ethacrynic acid.

Yet another objective of the present invention is to provide a crystalline t-butylamine salt of Ethacrynic acid.

Yet another objective of the present invention is to provide Ethacrynic acid having a purity of greater than or equal to 99% w/w and a dimer impurity in an amount less than 0.2% w/w by HPLC or preferably less than 0.1% w/w by HPLC and a composition comprising the high purity Ethacrynic acid.

The main aspect of the present invention is to provide an improved process for preparing Ethacrynic acid of formula I, Formula I

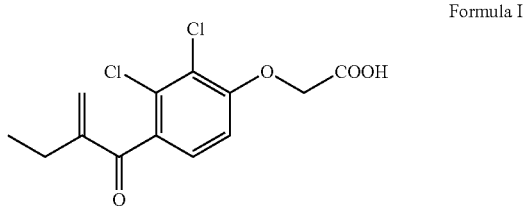 [SMILES: C=C(CC)C(=O)c1ccc(OCC(=O)O)c(Cl)c1Cl]

comprising the steps of:
(a) reacting 4-butyryl-2,3-dichloro-phenoxy acetic acid of formula II, Formula II

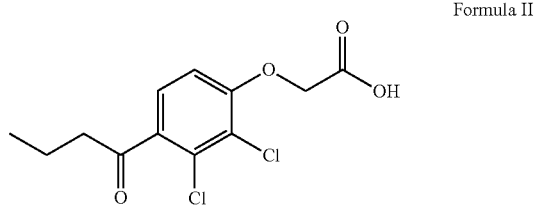 [SMILES: CCCC(=O)c1ccc(OCC(=O)O)c(Cl)c1Cl]

with dimethylamine or its salt to obtain [2,3-dichloro-4-[2-dimethylaminomethyl butyryl phenoxy acetic acid of formula III or its salt, Formula- III

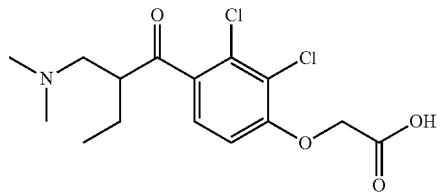

(b) hydrolysing [2,3-dichloro-4-[2-dimethylaminomethyl butyrylphenoxy acetic acid hydrochloride of formula III obtained in step a) with t-butyl amine to obtain t-butyl amine salt of Ethacrynic acid;
(c) acidifying the t-butyl amine salt of Ethacrynic acid formed in step b) to obtain Ethacrynic acid of formula I; and
(d) optionally purifying the obtained Ethacrynic acid with a solvent mixture of alkyl acetate and hydrocarbon solvent.

Another aspect of the present invention is to provide a process for preparing t-butyl amine salt of Ethacrynic acid comprising the step of hydrolysing [2,3-dichloro-4-[2-dimethylaminomethyl butyrylphenoxy acetic acid hydrochloride of formula III or its salt, Formula- III

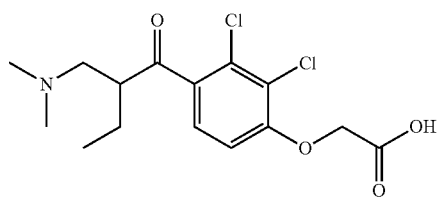

with t-butyl amine to obtain t-butyl amine salt of ethacrynic acid.

Yet another aspect of the present invention is to provide a process for preparing Ethacrynic acid of formula I, Formula I

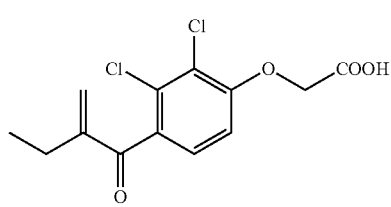

comprising the step of acidifying the t-butyl amine salt of Ethacrynic acid to obtain Ethacrynic acid of formula I.

Still another aspect of the present invention is to provide a process for preparing crystalline Ethacrynic acid of formula I,

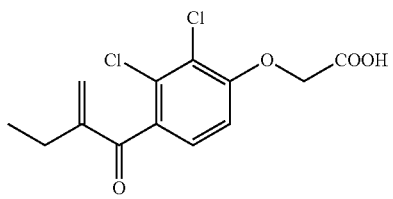

Formula I comprising the steps of:
(a) dissolving the ethacrynic acid with a solvent mixture of ester solvent and hydrocarbon solvent;
(b) optionally heating the solution; and
(c) cooling the solution obtained in step (a) or step (b) till the crystallization or the precipitation of the solid.

The above ester solvent is selected from a group comprising ethylacetate, isopropyl acetate, butyl acetate and mixtures thereof.

The above said hydrocarbon solvent is selected from a group comprising toluene, xylene, ethyl benzene and mixtures thereof.

Yet another aspect of the present invention is to provide a crystalline form of t-butylamine salt of Ethacrynic acid of formula I.

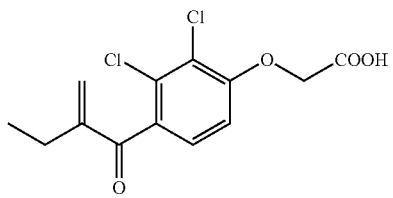

Formula I

The crystalline form of t-butylamine salt of Ethacrynic acid of formula I is characterized by 2θ peaks in the powder X-ray diffraction (PXRD) spectrum at about 6.6, 10.6, 12.9, 17.8, 18.3, 19.5, 24.4, 26.6, 27.9, and 31.2±0.2° degrees.

The crystalline form of t-butylamine salt of Ethacrynic acid of formula I is characterized by PXRD spectrum as shown in The FIGURE.

In another aspect the invention provides Ethacrynic acid having a purity of greater than or equal to 99% w/w and a dimer impurity in an amount less than 0.2% w/w by HPLC. In another aspect the invention provides Ethycrynic acid having a purity of greater than or equal to 99% w/w and a dimer impurity in an amount less than 0.1% w/w by HPLC.

In a further aspect, the invention provides a composition comprising above highly pure Ethacrynic acid.

BRIEF DESCRIPTION OF THE DRAWING

The FIGURE illustrates a powder X-ray Diffractogram (PXRD) of crystalline t-butylamine salt of Ethacrynic acid according to the principles of the present invention.

DESCRIPTION OF THE INVENTION

In one embodiment of the present invention is to provide a process to preparing Ethacrynic acid of formula I,

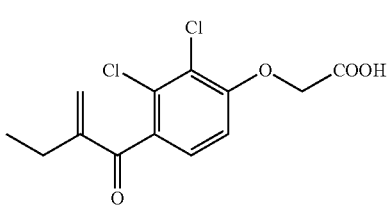

Formula I comprising the steps of:
(a) reacting 4-butyryl-2,3-dichloro-phenoxy acetic acid of formula II,

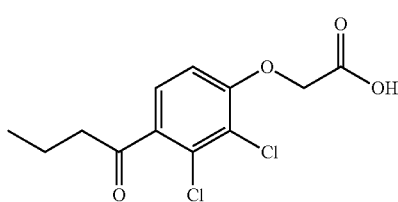

Formula II with dimethylamine or its salt to obtain [2,3-dichloro-4-[2-dimethylaminomethyl butyrylphenoxy acetic acid of formula III or its salt;

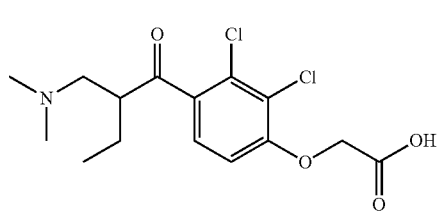

Formula- III (b) hydrolysing [2,3-dichloro-4-[2-dimethylaminomethyl butyrylphenoxy acetic acid hydrochloride of formula III obtained in step (a) with t-butyl amine to obtain t-butyl amine salt of ethacrynic acid;
(c) acidifying the t-butyl amine salt of ethacrynic acid formed in step (b) to obtain Ethacrynic acid of formula I; and
(d) optionally purifying the obtained Ethacrynic acid with a solvent mixture of alkyl acetate and hydrocarbon solvent.

The 4-butyryl-2,3-dichloro-phenoxy acetic acid of formula II is obtained by first preparing 2,3-dichloro-4-hydroxybutyrophenone, which is further treated with potassium carbonate followed by with Ethyl bromoacetate to obtain formula II.

The reaction of 4-butyryl-2,3-dichloro-phenoxy acetic acid of formula II with dimethylamine or its salt as in step (a) may be carried out in the presence of formaldehyde.

The reaction of 4-butyryl-2,3-dichloro-phenoxy acetic acid of formula II with dimethylamine or its salt as in step (a) may be carried out in the suitable aprotic polar solvent such as N,N-dimethylformamide, N-methylpyrrolidone and dimethyl sulfoxide.

The use of t-butylamine to form a t-butylamine salt of ethacrynic acid during the process for the preparation ethacrynic acid instead of alkali as a base reduces the formation of dimer impurity during the process thereby increasing the yield and purity of the API.

Ethacrynic acid prepared by one of the processes described in the present invention, is characterized by its purity ≥99% w/w by HPLC, preferably ≥99.5% w/w.

Commercially available ethacrynic acid samples and ethacrynic acid prepared by prior art processes contain the dimer impurity more than 1.3% w/w. Ethacrynic acid prepared by one of the processes described in the present invention contains less than 0.2% w/w of dimer impurity by HPLC, preferably less than 0.1% w/w of dimer impurity.

Another embodiment of the present invention is to provide a process for preparing t-butyl amine salt of ethacrynic acid of formula-I, Formula I comprising the step of hydrolysing [2,3-dichloro-4-[2-dimethylaminomethyl butyrylphenoxy acetic acid hydrochloride of formula III or its salts, Formula-III with t-butyl amine to obtain t-butyl amine salt of ethacrynic acid.

The step of obtaining t-butyl amine salt of ethacrynic acid from [2,3-dichloro-4-[2-dimethylaminomethyl butyrylphenoxy acetic acid hydrochloride may be carried out in suitable solvent or its mixtures selected from the polar aprotic solvent such as dichloromethane, dichloroethane, N,N-dimethylformamide, N-methylpyrrolidone, dimethyl sulfoxide or an aromatic hydrocarbon such as toluene, xylene and ethylbenzene.

Yet another embodiment of the present invention is to provide a crystalline form of t-butylamine salt of Ethacrynic acid of formula I characterized by 2θ peaks in the powder X-ray diffraction spectrum at about 6.6, 10.6, 12.9, 17.8, 18.3, 19.5, 24.4, 26.6, 27.9, and 31.2±0.2° degrees. The X-ray diffractogram of the crystalline t-butylamine salt of Ethacrynic acid is depicted in The FIGURE.

Still another embodiment of the present invention is to provide a process for preparing Ethacrynic acid of formula I Formula I comprising the step of acidifying t-butyl amine salt of ethacrynic acid to obtain Ethacrynic acid of formula I.

The step of acidifying t-butyl amine salt of ethacrynic acid may be done adding any inorganic acid. Said inorganic acid are selected from the group including hydrochloric acid, sulphuric acid or nitric acid.

The preparation of ethacrynic acid from the t-butyl amine salt of ethacrynic acid is carried out in suitable polar solvent. The polar solvent is selected from the group comprising ethyl acetate, water, methanol, ethanol, n-propanol or iso-propanol or its mixtures thereof.

Still another embodiment of the present invention is to provide a process for preparing crystalline ethacrynic acid of formula I, Formula I comprising the steps of:
(a) dissolving the ethacrynic acid with a solvent mixture of ester solvent and hydrocarbon solvent;
(b) optionally heating the solution; and
(c) cooling the solution obtained in step (a) or step (b) till the crystallization or the precipitation of the solid.

The ester solvent as mentioned the step (a) for dissolving of ethacrynic acid is selected from the group including ethyl acetate, isopropyl acetate, butyl acetate and mixtures thereof. The hydrocarbon solvent as mentioned the step (a) for dissolving of ethacrynic acid is selected from the group including toluene, xylene, and ethylbenzene and mixtures thereof.

The dissolving the ethacrynic acid with a solvent mixture of ester solvent and hydrocarbon solvent to get a clear solution may be done by heating to temperature of about 30° C. to 80° C., preferably at 35-70° C.

The purification of ethacrynic acid may also be done by leeching with solvent or a mixture of solvents containing an ester solvent, hydrocarbon solvent or its mixtures thereof.

A crystalline form of t-butylamine salt of Ethacrynic acid of formula I, characterized by 2θ peaks in the powder X-ray diffraction (PXRD) spectrum at about 6.6, 10.6, 12.9, 17.8, 18.3, 19.5, 24.4, 26.6, 27.9, and 31.2±0.2° degrees.

A crystalline form of t-butylamine salt of Ethacrynic acid of formula I, characterized by PXRD spectrum as shown in The FIGURE.

In another aspect the invention provides Ethacrynic acid having a purity of greater than or equal to 99% w/w and a dimer impurity in an amount less than 0.2% w/w by HPLC.

In another aspect the invention provides Ethycrynic acid having a purity of greater than or equal to 99% w/w and a dimer impurity in an amount less than 0.1% w/w by HPLC.

In a further aspect, the invention provides a composition comprising above Ethycrynic acid having a purity of greater than or equal to 99% w/w and a dimer impurity in an amount less than 0.2% w/w, preferably less than 0.1% w/w by HPLC.

The present invention is described by the following examples, which are for illustrative purpose only and should not be construed as to limit the scope of the invention in any manner.

EXAMPLES

Example 1: Preparation of 2,3-dichloro-4-hydroxybutyrophenone

To a mixture of anhydrous aluminium chloride (487.70 gm) and dichloromethane (5000 ml), 2,3-dichloroanisole (500 gm) was added at 30° C. and stirred for 10 min at the same temperature. This reaction mass was cooled to 20° C., then butyryl chloride (389.5 g) was slowly added at 25° C. and stirred the reaction mixture for 8 hours at 30° C. The progress of the Freidel Craft reaction was monitored by HPLC. Anhydrous Aluminium chloride (487.70 gm) was added to the reaction mass at 30° C. and stirred the reaction mass for 8 hours at 42° C. The progress of demethylation reaction was monitored by HPLC. After completion of the reaction, the reaction mass was cooled to 5° C. and water (2500 ml) was slowly added to the reaction mass at 15° C. The reaction mass was then distilled atmospherically for dichloromethane and under vacuum at 55° C. to obtain a concentrated residue. The concentrated residue was mixed with water (1500 ml) and toluene (1000 ml) at 55° C., cooled to 30° C. and stirred for 4 hours at 30° C. The resultant solid was filtered, washed with water (1000 ml) and dried for 2 hours at 30° C. The solid was further dried at 55° C. under vacuum for about 8 hours. Yield: 83.7%

Example 2: Preparation of 4-butyryl-2,3-dichloro-phenoxy acetic acid

Potassium carbonate (741.10 gm) was added to a slurry of 1-(2,3-dichloro-4-hydroxy phenyl)-butan-1-one (500.00 gm) in ethanol (4000 ml) at 30° C. and stirred for 20 minutes at the same temperature. Ethyl bromoacetate (716.46 gm) was added to the reaction mass at 30° C. and heated to 83° C. The reaction mixture was stirred for 12 hours at 83° C. The progress of the reaction was monitored by HPLC. After the completion of the reaction, ethanol in the reaction mass was distilled at 80° C. under atmospheric pressure. The residue was mixed with water (6500 ml) at 80° C. and stirred at 80° C. to get a clear solution. The obtained solution was cooled to 60° C. and then the pH of the solution was adjusted to 3.0 to 4.0 using 15% dilute hydrochloric acid at the same temperature. The resultant solid was filtered, washed with water (2000 ml) and dried at 50° C. under vacuum for about 8 hours. Yield: 92%.

Example 3

(a) Preparation of [2,3-dichloro-4-[2-dimethylaminomethyl butyrylphenoxy acetic acid: The solid obtained in example 2 (200 gm) was suspended in dimethyl formamide (500 ml). An aqueous solution of formaldehyde (37%, 82.51 gm) and dimethylamine hydrochloride (190.43 gm) was added into the reaction mass at 30° C. and stirred for 10 min at the same temperature. Then acetic acid (500 ml) and toluene (2000 ml) was added to the reaction mass and heated to 100° C. The reaction mixture was stirred for 12 hours at 100° C. The progress of the reaction was monitored by HPLC. After the completion of the reaction, the reaction mass was cooled to 30° C. Water (2000 ml) was added to the cooled reaction mass and the resultant biphasic mixture was stirred for 20 minutes. Organic layer containing the compound 2,3-dichloro-4-[2-dimethylamino methyl butyrylphenoxy acetic acid was separated.

(b) Preparation of t-butylamine salt of Ethacrynic acid: To the organic layer containing the compound 2,3-dichloro-4-[2-dimethylaminomethyl butyrylphenoxy acetic acid obtained in Example 3(a), tertiary butyl amine (75.36 gm) was added drop wise at a temperature of 20° C. and stirred for 5 hrs at 30° C. The resultant solid was filtered, washed with toluene (400 ml) and dried. Yield: 93%.

Example 4: Preparation of Ethacrynic Acid

Ethyl acetate (1000 ml) was added to a slurry of product obtained in Example 3 in water (1000 ml) at 30° C. and stirred for 10 minutes at the same temperature. The pH of the reaction mass was adjusted to 2.0 to 3.0 using 10% aqueous hydrochloric acid and stirred for 30 minutes at 30° C. The reaction mass was allowed to settle for layer separation. The organic layer was separated, washed with water (1000 ml) and distilled under vacuum. The obtained residue after distillation was mixed with cyclohexane (1600 ml) at 40° C. and then distilled to get a concentrated solution. The obtained concentrated solution was cooled to 35° C. and stirred for hours at 30° C. The resultant solid was filtered, washed with cyclohexane (4000 ml) and dried under vacuum. Yield: 60.1%; Purity by HPLC: 99.83% w/w; Content of dimer impurity: 0.07% w/w.

Example 5: Purification of Ethacrynic Acid

The product obtained in Example 4 was added to a mixture of toluene (510.00 ml) and ethyl acetate (90 ml) at 30° C. and heated to 65° C. Then the contents were maintained at 68° C. to get clear solution; stirred for 60 minutes at 65° C.; and cooled to 30° C. The cooled mass was maintained for 2 hrs at the same temperature and further cooled to 5° C. The resultant solid was filtered, washed with a chilled mixture of toluene (170 ml) and ethyl acetate (300 ml) and dried 1 hour at 30° C. Yield: 80.0%; Purity by HPLC: 99.74% w/w; Content of dimer impurity: 0.09% w/w.

Example 6: Purification of Ethacrynic Acid

The product obtained in Example 4 was added in to pre-heated mixture of toluene (255.00 ml) and ethyl acetate (45 ml) at 65° C. and heated to 68° C. stirred for 60 minutes and cooled to 5° C. The resultant solid was filtered, washed with a chilled mixture of toluene (170 ml) and ethyl acetate (300 ml) and dried. Yield: 80.0%.

We claim:
1. A process for preparing Ethacrynic acid of formula I,

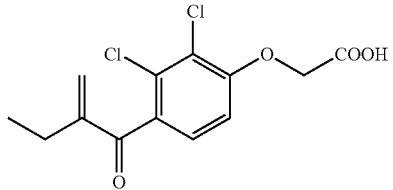

Formula I comprising the steps of:
(a) reacting 4-butyryl-2,3-dichloro-phenoxy acetic acid of formula II,

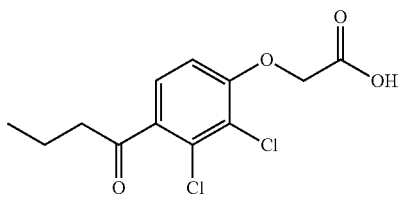

Formula II with dimethylamine or a salt thereof in the presence of formaldehyde to obtain [2,3-dichloro-4-(2-dimethylaminomethylbutyryl)phenoxy] acetic acid of formula III or a salt thereof,

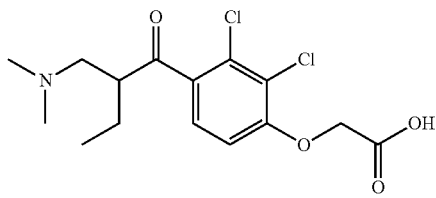

Formula- III (b) hydrolysing [2,3-dichloro-4-(2-dimethylaminomethylbutyryl)phenoxy] acetic acid hydrochloride of formula III obtained in step a) with t-butyl amine to obtain t-butyl amine salt of Ethacrynic acid;
(c) acidifying the t-butyl amine salt of Ethacrynic acid formed in step b) to obtain Ethacrynic acid of formula I; and
(d) optionally, purifying the obtained Ethacrynic acid with a solvent mixture of alkyl acetate and hydrocarbon solvent.

2. A process for preparing t-butyl amine salt of Ethacrynic acid comprising the step of hydrolysing [2,3-dichloro-4-(2-dimethylaminomethylbutyryl)phenoxy] acetic acid hydrochloride of formula III or a salt thereof,

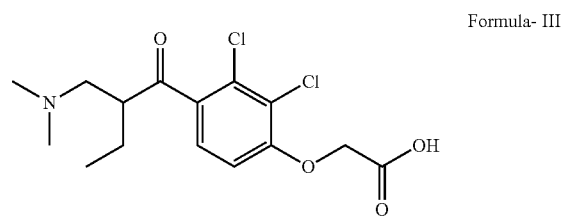 [SMILES: CCC(CN(C)C)C(=O)c1ccc(OCC(=O)O)c(Cl)c1Cl]

Formula- III with t-butyl amine to obtain t-butyl amine salt of Ethacrynic acid.

3. A process for preparing Ethacrynic acid of formula I,

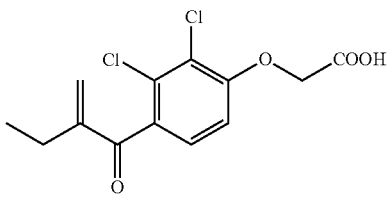

Formula I comprising the step of acidifying the t-butyl amine salt of Ethacrynic acid to obtain Ethacrynic acid of formula I.

* * * * *